United States Patent [19]

Haas et al.

[11] 4,417,143

[45] Nov. 22, 1983

[54] APPARATUS FOR DRIVING A RADIATION DETECTOR

[75] Inventors: Werner J. Haas, Inverness; Frank C. Scribano, Western Springs, both of Ill.

[73] Assignee: Siemens Gammasonics, Inc., Des Plaines, Ill.

[21] Appl. No.: 273,446

[22] Filed: Jun. 15, 1981

[51] Int. Cl.³ .............................................. G01T 1/20
[52] U.S. Cl. ................................................. 250/363 S
[58] Field of Search ............ 250/363 S, 361 R, 363 R; 378/179, 181, 195, 196

[56] References Cited

U.S. PATENT DOCUMENTS

| | | | |
|---|---|---|---|
| 3,011,057 | 11/1961 | Anger | 250/363 S |
| 3,281,598 | 10/1966 | Hollstein | 378/196 |
| 3,732,419 | 5/1973 | Kulberg et al. | 250/366 |
| 3,756,549 | 9/1973 | Lange | 248/123.1 |
| 3,984,689 | 10/1976 | Arseneau | 250/369 |
| 4,150,297 | 4/1979 | Borggren | 378/181 |
| 4,216,381 | 8/1980 | Lange | 250/363 S |
| 4,220,861 | 9/1980 | Colombo et al. | 250/363 S |
| 4,223,222 | 9/1980 | Gray et al. | 250/363 S |

*Primary Examiner*—Janice A. Howell
*Attorney, Agent, or Firm*—Karl F. Milde, Jr.

[57] ABSTRACT

An improved emission computerized tomography (ECT) drive mechanism for an Anger-type scintillation camera is disclosed. A support arm, carrying the camera head at one end and a counterweight at the other, is mounted on a universal joint and driven about the joint by a crank. The crank comprises an acme-type screw and the arm attaches to the crank at a point distant from the joint by means of an acme nut. The tilt angle of the arm is varied by varying the position of the acme nut on the acme screw.

10 Claims, 14 Drawing Figures

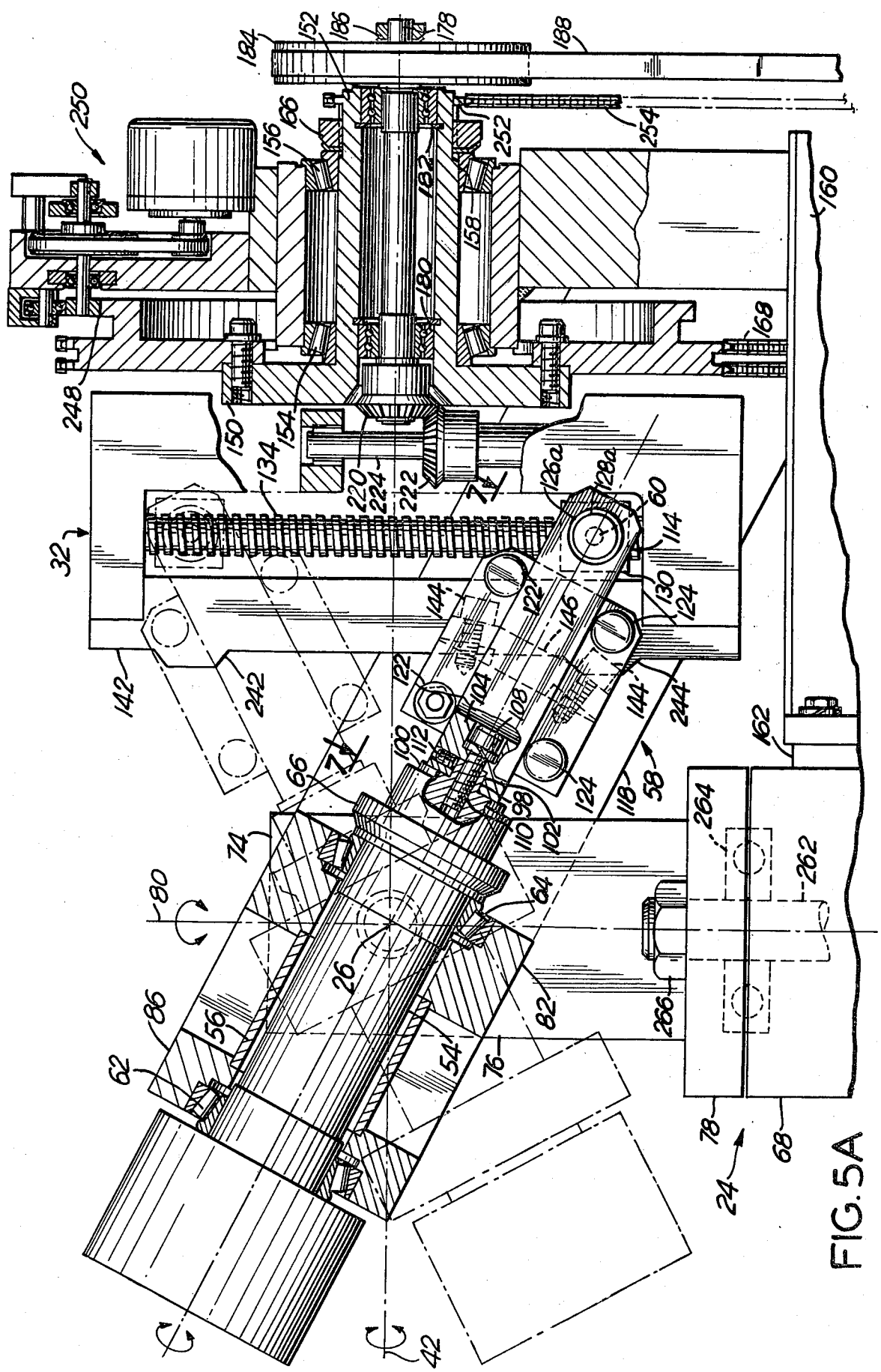

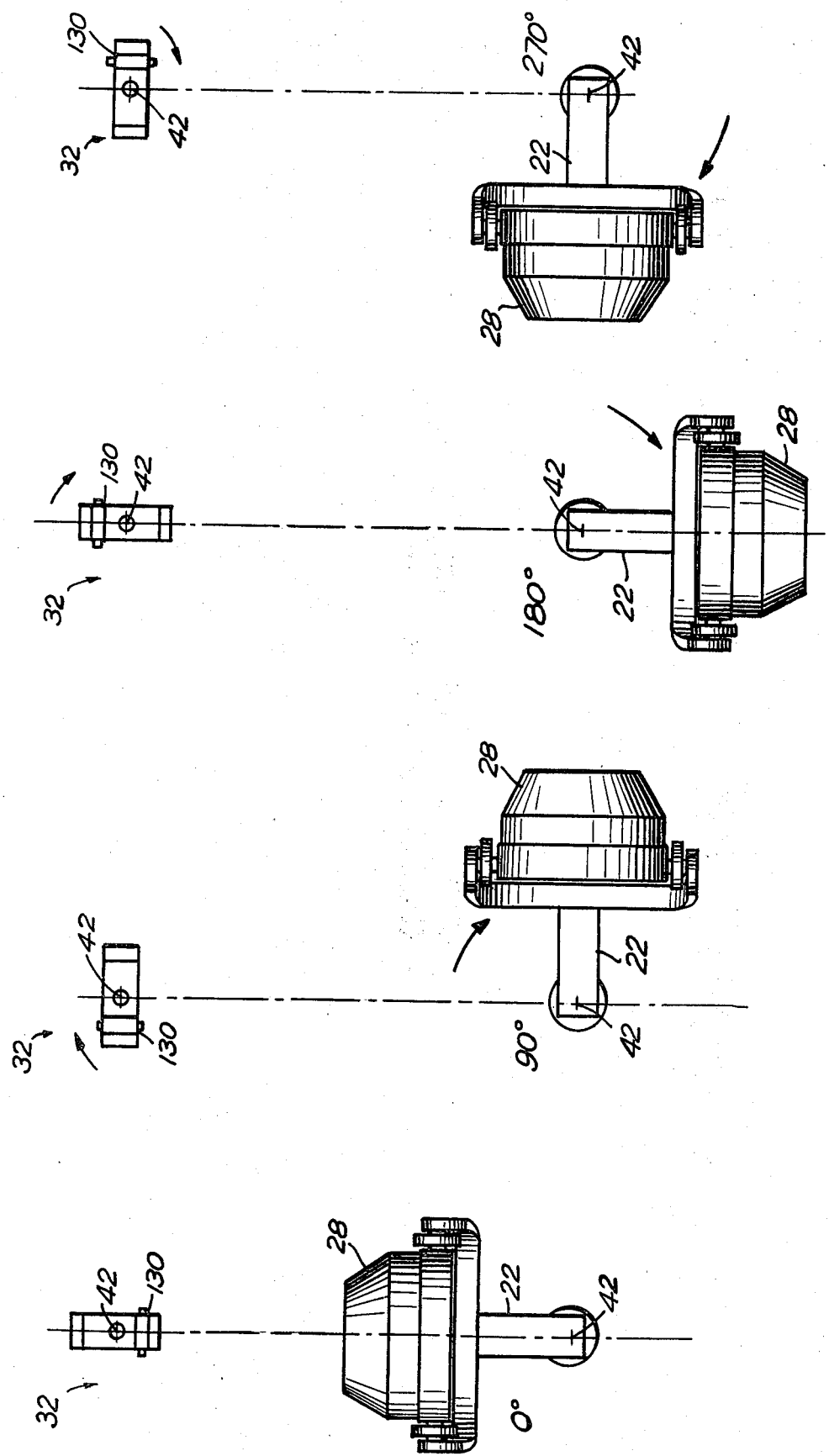

APPARATUS FOR DRIVING A RADIATION DETECTOR

BACKGROUND OF THE INVENTION

1. Field of the Invention

This invention relates to apparatus for driving a radiation detecting device for medical diagnostic purposes; and, especially, to apparatus for driving a scintillation camera to provide emission computerized tomography (ECT) capability for noninvasive medical diagnoses of a patient.

2. Description of the Prior Art

Emission computerized tomography is a noninvasive medical diagnostic procedure in which a head of a radiation detector precesses in an arc about a patient (for example, about the cranial-caudal axis of the patient), facing the part of the patient under study (e.g. a body organ) at all times. A commonly used radiation detector for ECT applications is an Anger-type scintillation camera (named for its inventor), the basic principles of operation of which are disclosed in U.S. Pat. Nos. 3,011,057; 3,732,419 and 3,984,689. The radiation detector computes the distribution of a radiation emitting substance previously ingested by the patient as detected from a plurality of viewing positions of the detector head, and analyzes this data to produce a profile of the object of study. In a typical ECT system, a single precession of the detector head about the patient produces a display showing the radioactive distribution in the object of study in a number of parallel section imaging planes.

Typical prior art structure is disclosed in U.S. Pat. No. 4,216,381. In that patent, a conventional, counterbalanced Anger-type scintillation camera is adapted for ECT analysis by structure which enables the camera head to be rotated in a circular orbit about a patient. The structure includes a base supporting an upright circular frame. The circular frame comprises an inner circular ring adapted for rotation within a concentric outer circular ring. Two parallel arms, tiltably attached at diametrically opposite balance points to the inner ring, carry the camera head at their one ends and a counterweight at their other ends. A drive system rotates the inner ring within the outer ring so that the points of attachment of the two arms to the frame are driven along a circular path whereby the detector head orbits the patient to receive emission data. The data is digitized and processed in electronic form. Using an appropriate algorithm, the computed radiographic distribution is constructed and displayed on a visual image display device. The radius of the arc which the head traverses is determined by the angle of tilt of the parallel arms at their points of attachment with respect to the inner ring. The angle of tilt is manually set and then locked prior to rotation by means of an electromagnetic brake. The manual setting of the tilt angle is aided by a pneumatic assist device connected between the inner ring and the arms adjacent the counterweight.

The prior art structure described in U.S. Pat. No. 4,216,381 is cumbersome and clumsy. Because the path of the head is controlled by parallel arms traveling about a ring, the apparatus is not compact and cannot be conveniently encased to give a pleasing aesthetic appearance which is important for patient ease in a hospital or doctor's office environment. Further, the points of attachment of the two arms that carry the head and the counterweight and also the brake that locks the tilt angle of the arms all rotate in a wide circle with the ring (the entire counterweight rotating about itself), thereby presenting increased risk of mechanical failure which may cause slipping and attendant inaccuracies in the data acquisition process or pose a safety hazard for the patient or the medical personnel in attendance.

SUMMARY OF THE INVENTION

It is an object of the present invention to provide an improved ECT drive mechanism for a scintillation camera that provides compact structure for driving the detector head in an orbital path with simple mechanical motions.

It is another object of this invention to provide an ECT drive system for a scintillation camera which includes an improved mechanism for controlling the size of the radius of the arc which the head traverses about the patient.

In accordance with one aspect of the invention, supporting structure is provided for driving a detector head of a radiation detector adapted for emission computerized tomography comprising an arm moveably mounted on a base at a fulcrum and supporting the detector head adjacent one end. Means are provided for driving the arm about the fulcrum so that the head traverses an arc about a patient, with the head always facing inwardly toward the patient. The motion of the head is such that a reference line drawn from the fulcrum to the head describes a conical surface having the fulcrum at its apex and the arc at its base. Means are provided for counterbalancing the movement of the arm about the fulcrum due to the weight of the head.

In a preferred embodiment described in detail below, the means for driving the arm about the fulcrum of the base comprises a crank rotatably mounted on the base and attached to the arm at a point displaced from the fulcrum. The crank drives the displaced point on the arm about the fulcrum so that the point traverses a second arc. The crank drives the displaced point in such a manner that a second reference line drawn from the fulcrum to the displaced point describes a second conical surface having the fulcrum at its apex and the second arc at its base.

In another aspect of the invention, means are provided for varying the tilt of the arm, i.e. the radius of the arc traversed by the detector head in its orbit about the patient. In the embodiment described below, in which the arm is driven about the fulcrum by means of a crank attaching to a point on the arm displaced from the fulcrum, the angle of tilt of the arm about the fulcrum is varied by means which vary the effective length of the crank.

There have thus been outlined rather broadly certain objects, features and advantages of the invention in order that the detailed description that follows may be better understood, and in order that the present contribution to the art may be better appreciated. There are, of course, additional features of the invention that will be described more fully hereinafter. Those skilled in the art will appreciate that the conception on which this disclosure is based may readily be utilized as the basis for the designing of other arrangements for carrying out the purposes of this invention. It is important, therefore, that this disclosure be regarded as including all such equivalent arrangements that encompass the spirit and scope of the invention.

BRIEF DESCRIPTION OF THE DRAWINGS

An embodiment of the invention has been chosen for purposes of illustration and description, and is shown in the accompanying drawings forming a part of the specification, wherein:

FIGS. 5A and 5B together form a detailed composite side elevation view of the drive mechanism of the structure of FIG. 1, shown partially in cross section;

FIGS. 10A–10D are schematic representations useful in understanding the principles of operation of the structure of FIG. 1.

Throughout the drawings, like elements are referred to by like numerals.

DESCRIPTION OF THE PREFERRED EMBODIMENT

Figure 1:
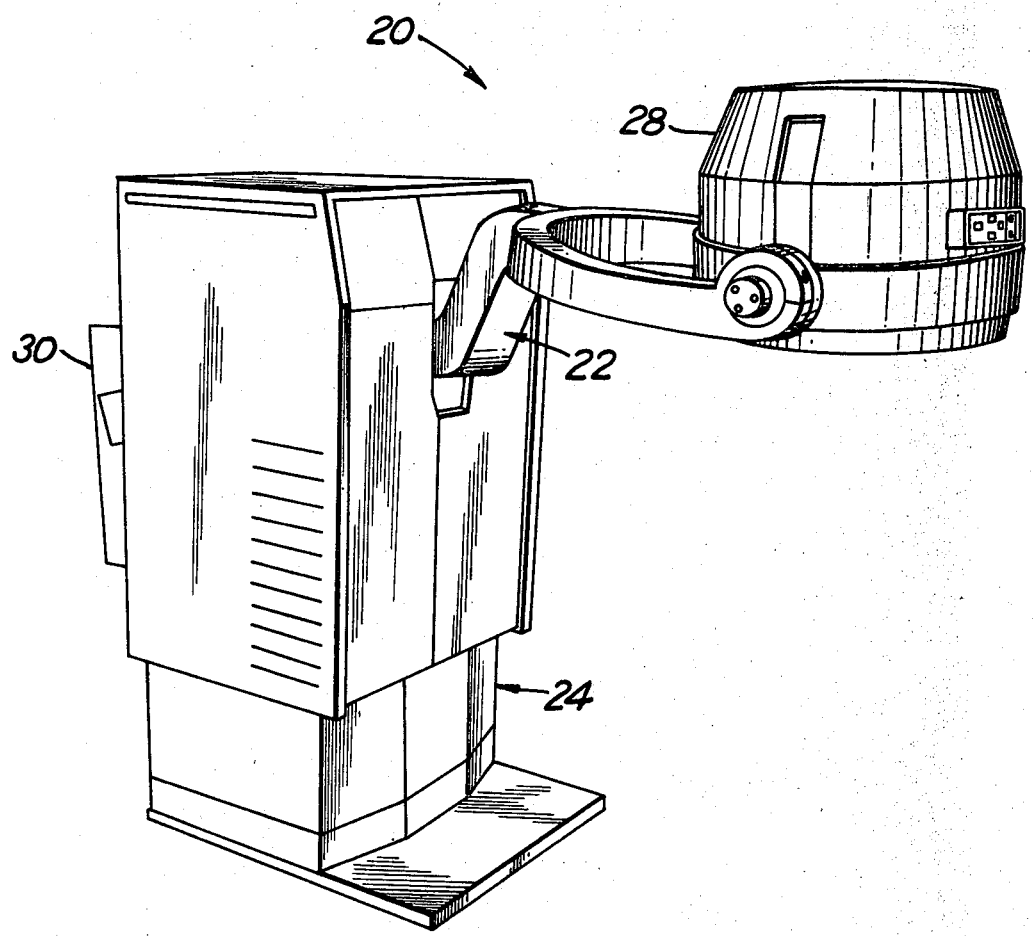
FIG. 1 is an overall perspective view of the supporting structure for driving a detector head of a radiation detector adapted for emission computerized tomography in accordance with an embodiment of the present invention.

The overall structure of an Auger-type gamma camera 20 adapted for emission computerized tomography is shown in FIGS. 1–4. A support arm 22 is moveably mounted to a base 24 at a fulcrum support point 26 (referred to by the letter A in FIG. 2). A detector head 28 is mounted at one end of arm 22 and a counterweight 30 mounted at the other end of the arm 22 serves as means for counterbalancing the moment of the arm 22 about the fulcrum 26 due to the weight of the head 28. A crank 32 (shown schematically in FIG. 2 and indicated in FIGS. 3 and 4), discussed in greater detail below with respect to FIG. 5A, is mounted on the base 24 and attaches to the arm 22 at a point designated by reference letter B in FIG. 2 which is displaced from the fulcrum 26. The crank has an effective length equal to the distance from the displaced point (designated by the letter B) and the point of rotational mounting on the base 24 (designated by the letter O in FIG. 2).

Figure 2:
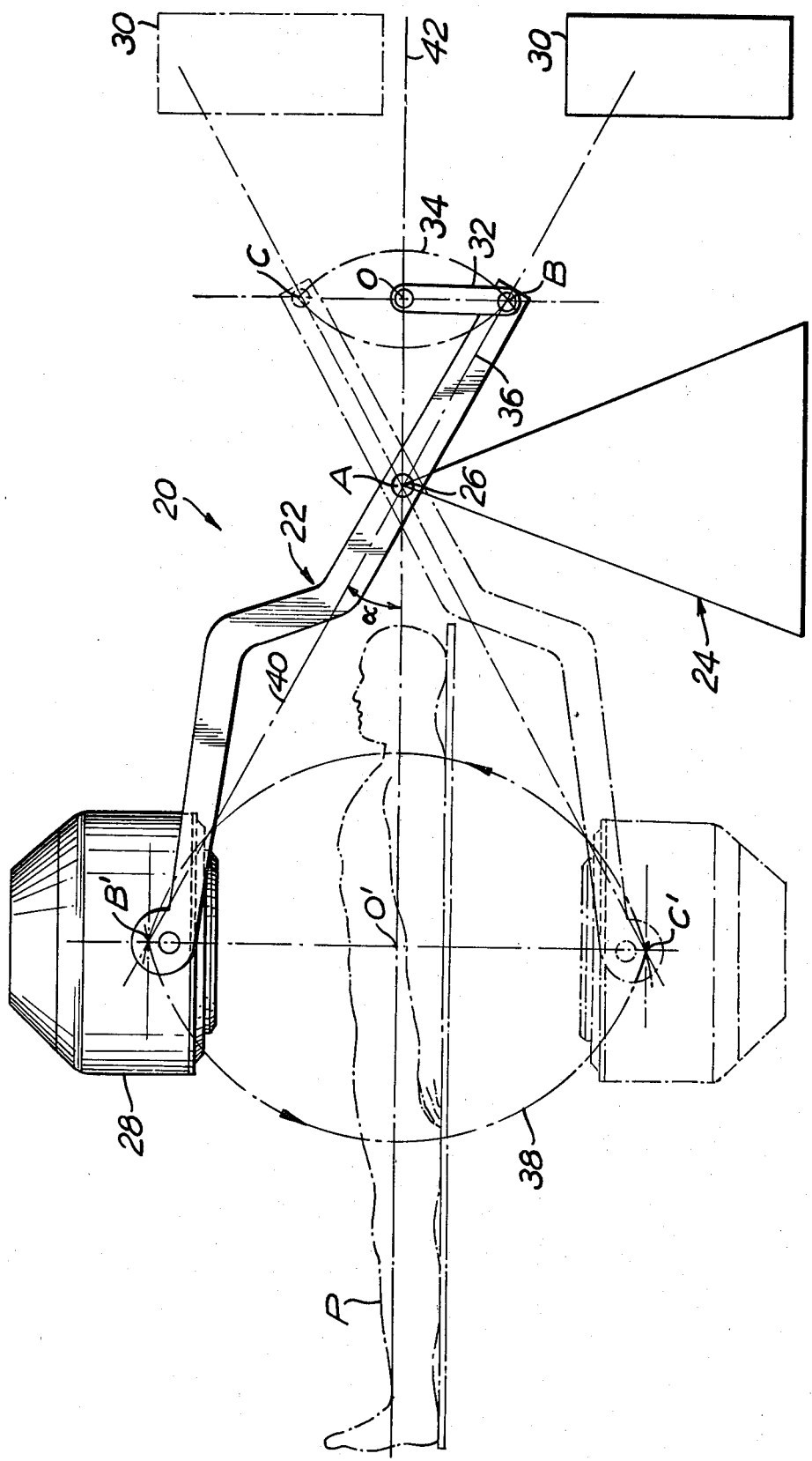
FIG. 2 is a schematic representation of the supporting structure of FIG. 1.

As more fully described below, the crank 32 serves to drive the point B about the fulcrum 26 so that the point B on arm 22 traverses an arc 34 (see FIG. 2). This causes a reference line 36 drawn from the fulcrum 26 (point A in FIG. 2) to the point B to describe a conical surface whose apex is at point A and whose base is defined by arc 34. This rotation of the crank 32 causes the detector head 28 to likewise be driven about the fulcrum 26 so that the head 28 traverses an arc 38 (FIG. 2) with the head 22 facing inward about a patient P. This movement of the head 28 is such that a reference line 40 drawn from the fulcrum 26 to the head 28 describes a conical surface with its apex at the fulcrum 26 and its base defined by the arc 38. As shown in FIG. 2, the conical surfaces described by reference lines 36 and 40 for one complete revolution of the crank 32 about point O are two cones positioned with their respective apexes at point A (fulcrum 26) and their central axes coincident along an axis 42. The patient P is positioned with respect to the structure 20 and the axis 42 so that the head 28 precesses roughly about the cranial-caudal axis of patient P. The angle $\alpha$ (FIG. 2) between the reference line 40 and the axis 42 is the angle of tilt of the structure 20 and relates to the radius O'-B' of the arc 38, that is, the height of the detector head 28 above the patient P. The angle $\alpha$ and, thus, the distance O'-B' is determined by the effective length O-B of the crank 32, which is the distance from the displaced point B to the center of the arc 34. Since the cones mapped by the respective reference lines 36 and 40 during one complete revolution of the detector head 28 are similar cones, it will be appreciated that varying the effective length of the crank 32 (to give a different tilt angle $\alpha$) will produce a corresponding variation in the height O'-B' of the detector head 28 above the patient P.

Figure 3:
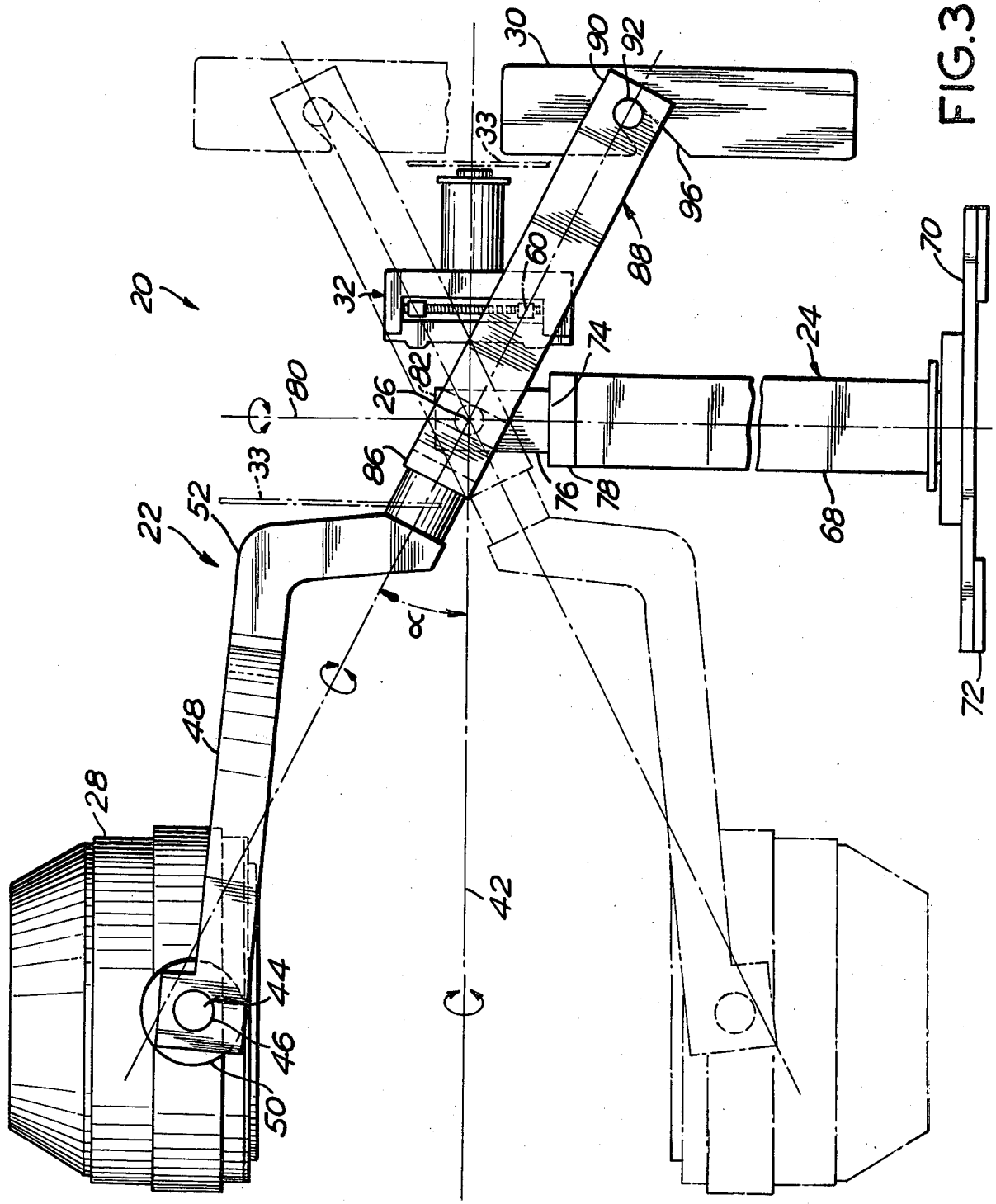
FIG. 3 is a simplified side elevation view (with the casing removed) of the structure of FIG. 1.
Figure 4:
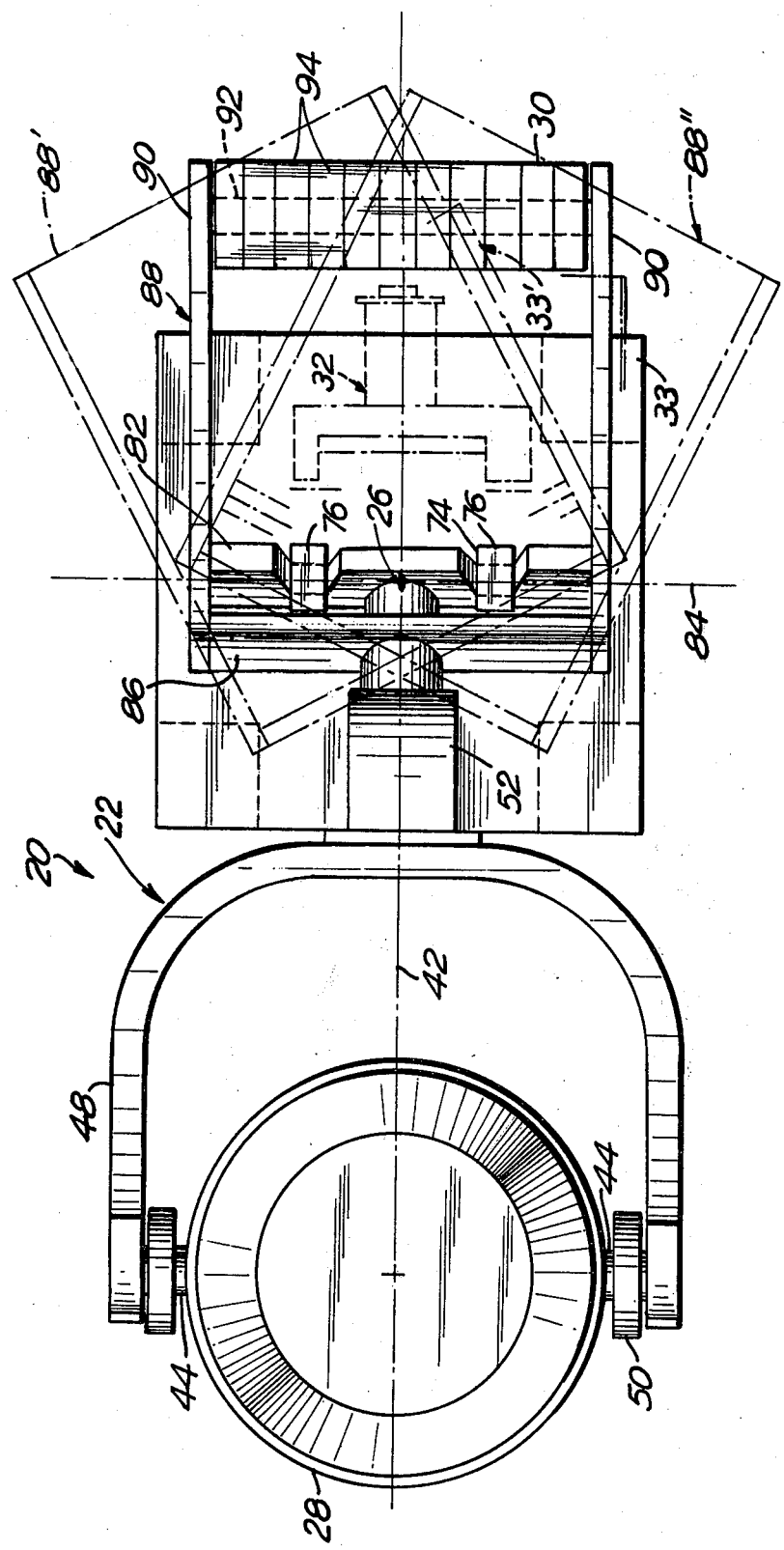
FIG. 4 is a top plan view of the structure of FIG. 3.

The detector head 28 is pivotally mounted on an end of support arm 22 by means of trunnions 44 (FIG. 4) which are received in eyes 46 (FIG. 3) of a yoke 48 portion of the support arm 22. Hand-operated disc brake 50 serves to lock the position of the detector head with respect to the yoke 48. The two bifurcations of yoke 48 merge at a point which is attached to the top of a goose neck 52. The lower end of goose neck 52 is fixedly mounted onto a yoke rotate shaft 54 which extends through a sleeve 56 and fastens by means of a telescoping coupling member 58 (see FIG. 5A) to a point of attachment 60 on the crank 32. The yoke rotate shaft 54 is received within sleeve 56 for rotation with respect thereto on tapered roller bearings 62 and 64 (FIG. 5A). A collar 66 secures the yoke rotate shaft 54 within the sleeve 56. As seen in FIG. 3, the base 24 comprises a vertical column 68 mounted on a support member 70 having pads 72. A U-shaped saddle 74 having two side members 76 joined by a crosspiece 78 is swivelly mounted atop the column 68 for rotation about the column axis 80. The sleeve 56 is clamped between beam member 82 and 86 and trunnioned between the side members 76 of the saddle 74 for pivoting up and down about a trunnion axis 84 (FIG. 4). The mounting arrangement wherein arm 22 is rotatably received within the sleeve 56; the sleeve 56 is pivotally received between the side members 76 of the saddle 74; and the saddle 74 is swivelly mounted atop the column 68 provides a universal joint connecting the arm 22 atop the base 24. The point of support 26 (signified by letter A in FIG. 2) thus holds the arm atop the base 24 in a manner which resembles the way in which an oar is held in an oar lock on a boat.

A front beam member 86 extends at right angles to the sleeve 56 and forms the front portion of a box frame 88 (see FIG. 4) which supports the counterweight 30 and serves as means for counterbalancing the moment of the arm 22 about the fulcrum 26 due to the weight of the head 28. In addition to the front beam member 86, the box frame 88 includes two parallel side elements 90 and a counterweight support bar 92. As seen in FIG. 4, the counterweight 30 is made up of sections 94 having cut out channels 96 (FIG. 3) which slip over the support bar 92. Since the counterweight is heavy, the sectional construction permits the counterweight to be assembled at the installation site and eliminates the need to have a crane or pulley system available during assembly. Each section 94 is of a weight that can be lifted by a typical installation person.

Figures 7, 8:
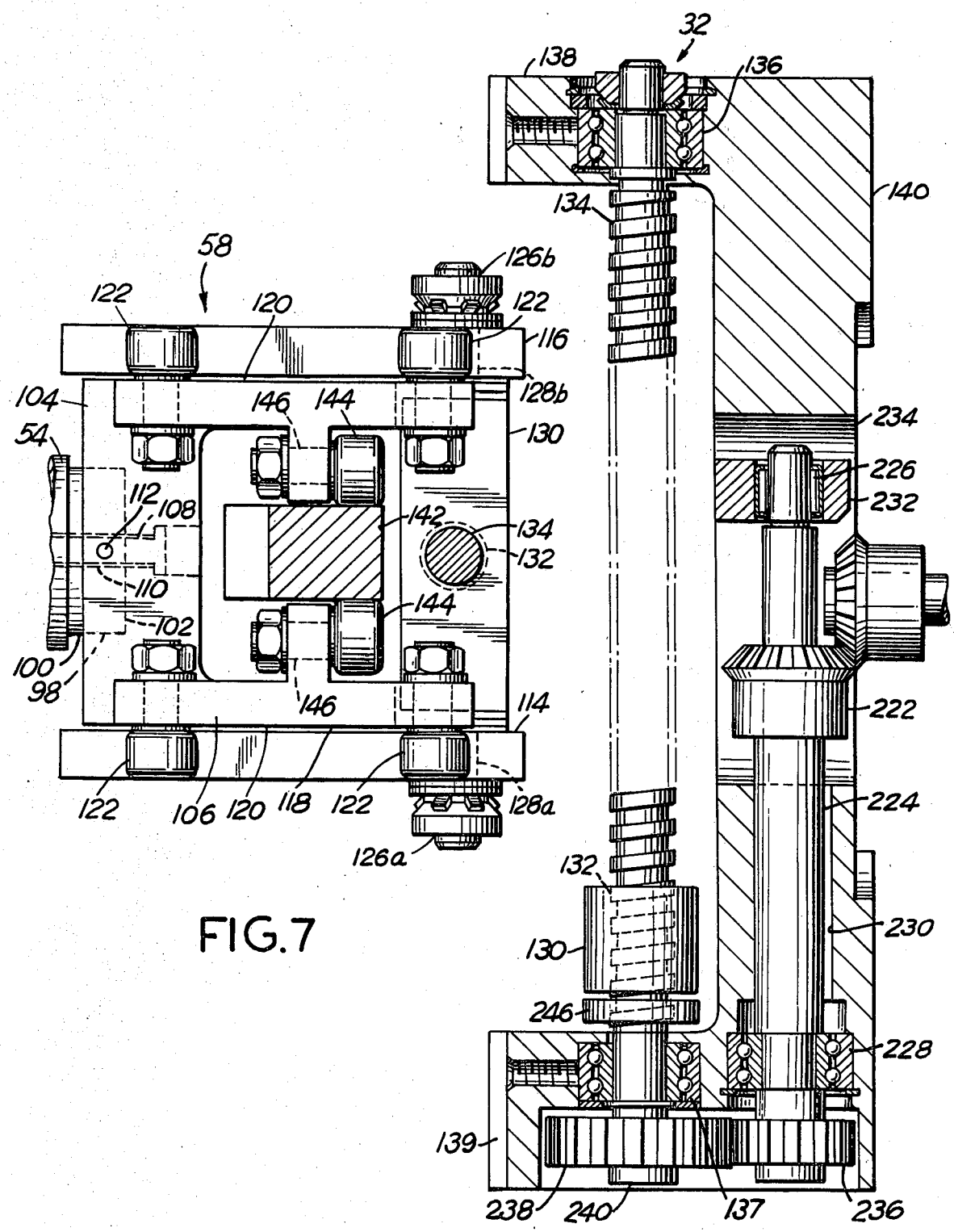
FIG. 7 is a section view taken along the line 7—7 of FIG. 5A.
FIG. 8 is a side view, partially in section, of the crank of FIG. 5A.
Figure 9:
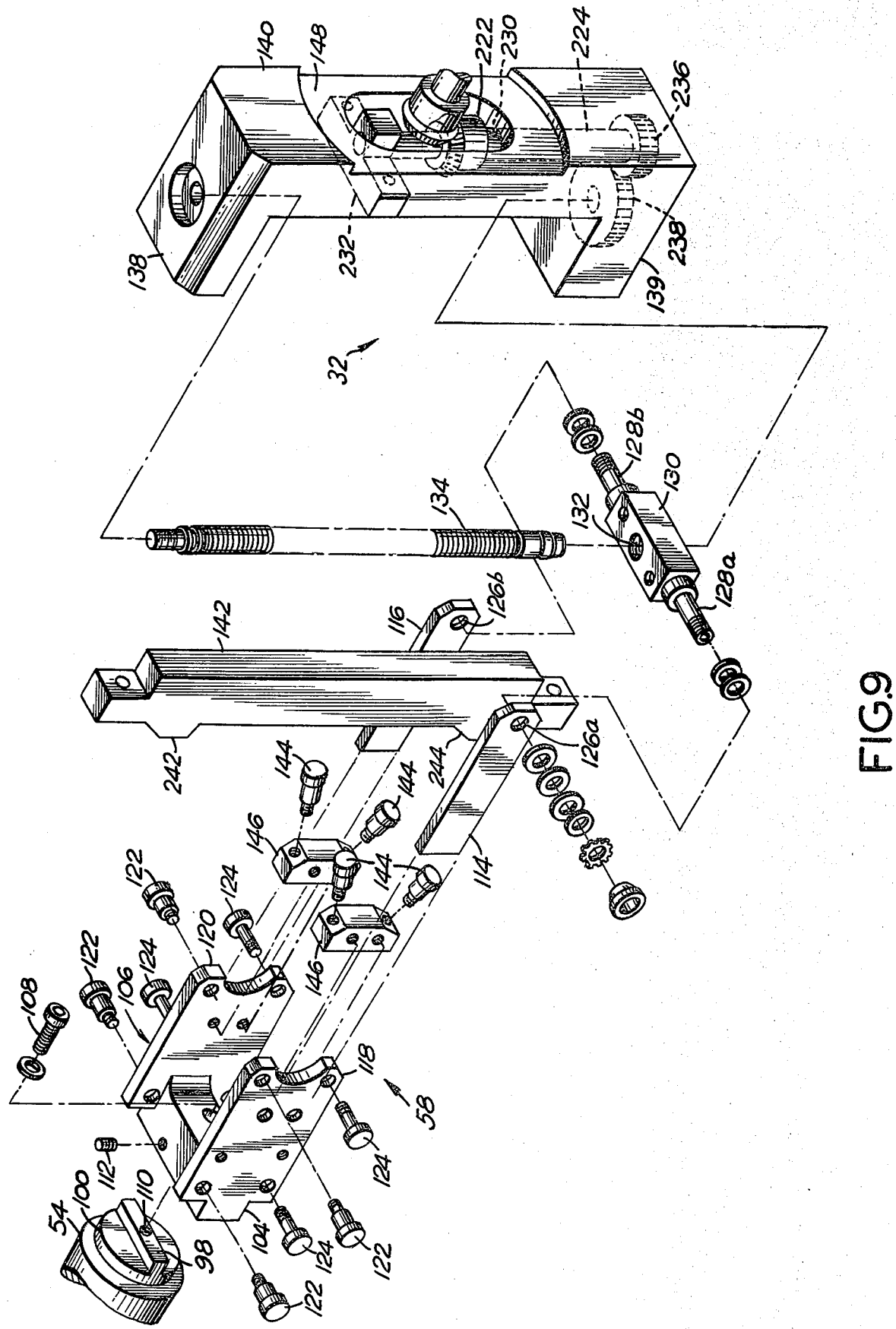
FIG. 9 is an exploded perspective view of the crank and coupling means of the structure of FIG. 5A.

The yoke rotate shaft 54 which extends through the sleeve 56 terminates in a tongue 98 (FIGS. 5A, 7 and 9) which extends diametrically across the end face of a smaller diameter end portion 100 of the rotate shaft 54. The tongue 98 is received within a complementary shaped recess 102 of a crosspiece 104 of a bifurcated member 106 of the telescoping coupling member 58. The relationship between the tongue 98 at the end of the yoke rotate shaft 54 and the groove or recess 102 of the bifurcated member 106 is maintained by a suitable fastening means such as threaded bolt 108 which projects into an internally threaded bore 110 in the rear of the shaft 54. The bolt 108 is secured against movement within the bore 110 by means of a set screw 112 which is tightened down against the bolt 108 from above as seen in FIGS. 7 and 9. The coupling member 58 includes slider plates 114 and 116 which are received adjacent to the sides 118 and 120 of the bifurcated member 106 and held adjacent thereto by means of adjustable cam rollers 122 and fixed cam rollers 124. The slider plates 114, 116 have eyes 126a and 126b which are respectively received onto pins 128a and 128b projecting laterally from the sides of acme nut 130 (FIG. 9). Acme nut 130 includes an internally threaded bore 132 which mates with an externally threaded acme screw member 134 which is supported by bearings 136 and 137 positioned within the upper and lower projections 138 and 139 of crank housing 140 (FIG. 8) of crank 32. Also supported between the projections 138 and 139 of crank housing 140 is a guide bar 142 which serves as a track for the cam rollers 144 attached to cam followers 146 which are mounted on the inside of the bifurcated member 106 of the telescoping coupling member 58 (FIG. 9).

Figure 5B:
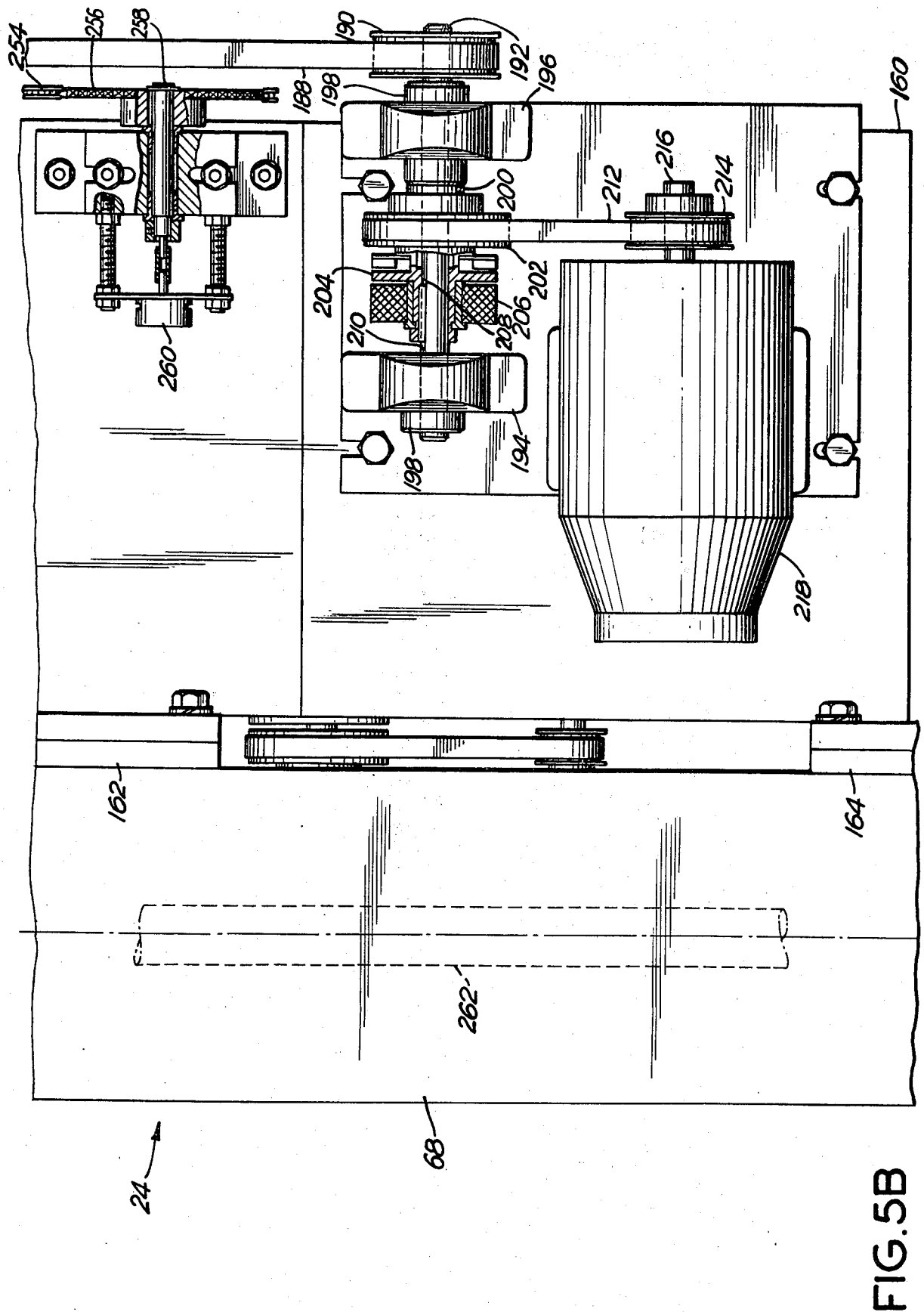
Figure 6:
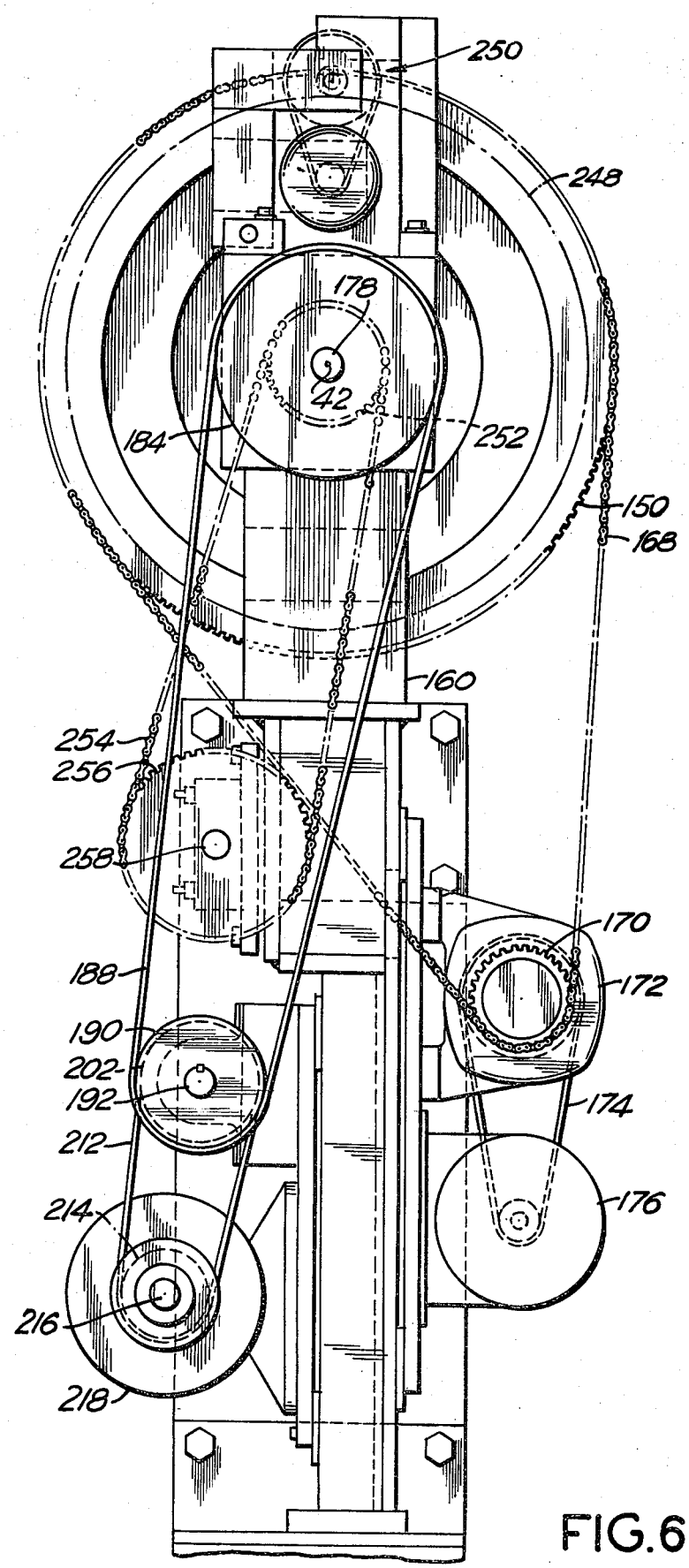
FIG. 6 is a back view of the drive mechanism of FIGS. 5A and 5B.

As seen in FIG. 9, the rear of the crank housing 140 includes an oval recess 148 into which a matching front portion of a double sprocket chain drive pulley 150 is received (FIG. 5A). The chain drive pulley 150 is formed integrally with a rotate drive shaft 152 which is supported on tapered roller bearings 154 and 156 within a bore 158 of weldment 160 which is mounted to the column 68 on mounting pads 162 and 164 (FIG. 5B). A lock ring 166 holds the rotate drive shaft 152 in position within bore 158 of the weldment 160. A double chain 168 (FIGS. 5A and 6) is threaded around the double sprocket of the pulley 150 and around the output sprocket 170 of a gear reducer 172. The gear reducer 172 is driven by means of a belt 174 which is driven by a DC motor rotate drive 176 (FIG. 6).

A tilt drive shaft 178 is rotatably received on needle bearings 180, 182 within the interior of the rotate drive shaft 152. At the right end (as viewed in FIG. 5A) of tilt drive shaft 178 is positioned a pulley 184 which is held in place by a lock nut 186. The pulley 184 is driven by a belt 188 which wraps around a pulley 190 positioned for rotation with a clutch output shaft 192. The clutch output shaft 192 is mounted on the weldment 160 by means of single pillow block bearings 194 and 196 and held in place by collars 198 (FIG. 5B). A flange type bronze bearing 200 serves as a mount for a pulley 202 which is part of a conventional clutch assembly. An electromagnetic clutch 204 having a coil 206 and a key 208 received within a key stock 210 on the clutch output shaft 192, provides for selective engagement and disengagement of the clutch, i.e. selective connecting and disconnecting of pulley 202 for rotating the clutch output shaft 192. Pulley 202 is driven by a belt 212 which rotates with the movement of a pulley 214 attached for rotation on a drive shaft 216 of a tilt drive DC motor 218.

On the left end of tilt drive shaft 178 (as viewed in FIG. 5A) is positioned a bevel gear 220 which meshes with a bevel gear 222 mounted on a vertical bevel gear shaft 224 which is received for rotation on needle bearing 226 and bearing 228 within a cavity 230 of the crank housing 140 (FIG. 8). The needle bearing 226 is positioned on a crank insert 232 which is fixed into the opening 234 of the crank housing 140. At the bottom of the shaft 224 (see FIG. 8) is positioned a spur gear 236 which meshes with a spur gear 238 positioned by means of screw 240 onto the bottom of the acme screw 134. Rotation of the pulley 214 on the shaft 216 of the DC motor 218 when the clutch is engaged (FIG. 5B) will cause rotation of the pulley 184 and corresponding rotation of the tilt drive shaft 178 on the bearings 180 and 182 within the rotate drive shaft 152 (FIG. 5A). This will cause rotation of bevel gear 220 which meshes with bevel gear 222. When bevel gear 222 is rotated, the corresponding rotation of spur gear 236 (FIG. 8) will rotate spur gear 240 and cause rotation of the acme screw 134. Rotation of the acme screw 134 will drive the acme nut 130 in a direction along the axis of the acme screw 134 to a new position. This will correspond to a change in the effective length of the crank 32 between the axis 42 and the point 60 (FIGS. 3 and 5A). As the point 60 is moved, there will be a corresponding change in the tilt angle α of the yoke rotate shaft 54 with respect to the axis 42. As the acme nut 130 is driven toward the axis 42 through the rotation of the acme screw 134, the distance between the point of attachment 60 of the coupling member 58 to the crank 32 and the fulcrum or main pivot point 26 will be reduced. This shortening of the distance will be compensated for by the telescoping of the coupling member 58, as the slider plates 114 and 116 supported on cam rollers 122 and 124 move inward toward the end of the yoke rotate shaft 54. As the acme nut 130 moves up the acme screw 134, the cam rollers 144 supported on cam followers 146 will traverse an arc on the sides of the guide bar 142. The guide bar 142 is shaped with two trapezoidal projections 242 and 244 to accommodate the outer limits of travel of the cam rollers 144 as the acme nut 130 is moved from one extreme position on acme screw 134 to the opposite extreme position. A backup nut 246 (FIG. 8) increases the safety of the acme nut 130 as it moves in its course along the acme screw 134.

The pulley 150 is formed in its rear portion with a circular drum 248 (FIG. 5A) which friction drives a conventional shaft encoder 250 such as Data Technology Part No. RS-23C which is mounted on the weldment 160 and serves to provide an electrical signal designating the position of the pulley 150 in its rotation, and thus the position of the crank 32 and the detector head 28. The right end (FIG. 5A) of the rotate drive shaft 152 includes a sprocket 252 which drives a chain 254 connected to the pulley 256 (FIG. 5B) of a shaft 258 of a potentiometer 260. This potentiometer assembly serves as a backup to the conventional shaft encoder 250 to provide a visual indication of the position of the detector head in its rotation about the patient P during ECT drive. The operation of the structure can be briefly summarized as follows:

With the rotate drive motor 176 in the off position, the clutch assembly 204 is engaged and the tilt drive motor 218 energized to set the correct tilt angle α (see FIGS. 2, 5A, 5B and 6) of the detector head with respect to the patient P. As mentioned previously, the radius O'B' of the arc 38 (FIG. 2) which the detector head 28 traverses in its orbit around the patient P is a function of the radius OB of the arc 34 which the crank 32 traverses when it is driven. Thus, the tilt angle α and the distance O'B' from the detector head to the patient is varied by varying the position of the acme nut 130 (FIG. 5A) with respect to the axis 42. This changes the effective arm of the crank 32. The tilt drive motor 218 (FIG. 5B) is energized with the clutch 204 engaged so that the belt 188 drives the pulley 184 of tilt drive shaft 178 (FIG. 5A). Rotation of the tilt drive shaft 178 rotates the bevel gear 220 attached on the left end thereof. This produces corresponding rotation of bevel gear 222 which rotates the connected shaft 224 (FIG. 8) to rotate the spur gear 236. The rotation of spur gear 236 rotates the spur gear 238 which rotates the acme screw 134. The acme nut 130 is prevented from rotation by its connection to the slider plates 114 and 116. Thus the rotation of the acme screw 134 drives the nut 130 along the screw 134 to change the effective crank arm of the crank assembly 32. Rotation of the shaft 216 of motor 218 in one direction causes the nut 130 to travel up the screw 134; rotation of the motor 218 in the opposite direction drives the nut 130 down the screw 134. As the acme nut 130 moves from a position on the bottom of acme screw 134 to a position in the middle of the screw 134, the distance from the point of attachment 60 to the main pivot point 26 (FIG. 5A) is shortened. This shortening is accommodated by the telescoping coupling member 58 in which the slider plates 114 and 116 received on cam rollers 122 and 124 move toward the end of the rotating shaft 54. When the detector head 28 is at the desired position above the patient P, corresponding to the desired tilt angle α, the clutch 204 is disengaged, and the position of the nut 130 on the screw 134 is locked.

When the clutch has been disengaged, the rotate drive motor 176 (FIG. 6) is energized to drive the chain 168 to rotate the pulley 150 about the axis 42. The front end of the pulley 150 is shaped to be received into a correspondingly shaped recess of the crank housing 140. Thus, rotation of the pulley 150 rotates the crank 32 in a corresponding fashion. For clockwise movement of the crank 32, for example, the portion of the acme screw from its center to the point of attachment 60 acts as a rotating crank to drive the arm 22 about the fulcrum 26 so that the detector head 28 traverses a clockwise arc 38 (FIG. 2). Since the yoke rotate shaft 54 is rotatably received within sleeve 56, as the crank 32 is rotated, the yoke rotate shaft 54 is likewise rotated clockwise so that the head 28 always faces the patient P (FIG. 2). FIGS. 10A-10D illustrate the movement of the detector head 28 corresponding to the rotation of the crank 32. FIG. 10A shows the detector head in its 0° starting position above the patient, when the crank 32 is in the vertical position with the nut 130 below the axis 42. This position is shown in FIGS. 2-4 by solid lines. As the crank 32 rotates clockwise, the crank 32 is brought into a horizontal position with the nut 130 to the left of the central axis 42 when the structure 20 is viewed from the detector head side. This corresponds to the position shown in FIG. 10B, in which the detector head is in the 90° position. The position of the box frame 88 supporting the counterweight 30 when the detector head is in the 90° position shown in FIG. 10B is shown by the dot and dash line 88' in FIG. 4. For clarity, the casing 33 of the structure 20 is only shown in FIG. 1. However the position of the edge of the casing 33 when the box frame 88 is brought into the 90° position is shown at the reference numeral 33' in FIG. 4.

As the crank arm 32 continues to rotate, the detector head is brought into the 180° position, shown by the dot and dash lines in FIGS. 2 and 3. In this position, the crane 32 is vertical and the nut 130 is above the axis 42. The position of the casing or enclosure wall 33 when the head is at a 180° position is the same as it is in the 0° position since a vertical opening (see FIG. 1) permits the yoke rotate shaft 54 to assume the 180° position without moving the casing. And finally, as seen in FIG. 10D, the detector head is brought into a 270° position, with the box frame 88 taking a position as shown by the dot and dash line 88" in FIG. 4. In a preferred embodiment, the detector head 28 is moved clockwise (as viewed from the detector head side) 360° for one revolution and is then turned counterclockwise to bring it back to its starting point. Movement in this manner prevents the entanglement of electrical cables (not shown) which connect the detector head electronics with the data processing electronics.

An acme type thread is chosen for the nut 130 and screw 134 since it has a square crest thread form and profile angle that resists backdriving when subjected to load. This is desirable to ensure that the nut 130 does not vary from its selected position on screw 134, thereby changing the set tilt angle α, during rotation. The thread should be selected to have a slope that is less than 50 percent efficient. A preferred form of the acme screw 134 has a diameter of ¾-inches and a thread pitch of five threads per inch.

The crosspiece 78 of the U-shaped saddle 74 is fastened by any suitable means atop the vertical column 68 (FIGS. 3, 5A and 5B) so that it can freely swivel about the column axis 80. A preferred fastening means includes a tendon shaft 262 (FIGS. 5A, 5B) that runs the full length down the inside of the center of the column 68. The crosspiece 78 rests on the inner race of a tapered roller bearing 264, the outer race of which is mounted in a fixed position on top of the column 68. The tendon shaft 262 is coupled to the saddle 74 by a fastener 266 and engages a thrust bearing (not shown) at the base of the column 68 and clamps the whole column assembly into an integral configuration. The bearings are preloaded, with 3,000 pounds of tension being placed on the tendon shaft 262.

The rotate drive motor 176 (FIG. 6) can be a ⅛ HP, 1800 r.p.m. operating speed DC drive motor. The gear reducer 172 can be a harmonic gear reducer, such as commercially available from the USM Corp., Harmonic Drive Division, Part No. HDC 5C (200:1 reduction), which provides a reduction of 1800 r.p.m. to ½ r.p.m. of the operating speed. The motor and pulley drive ratios are preferably selected to provide slow and fast rotation speeds of the detector head 28 about the patient of one revolution in 20 minutes and one revolution in 2 minutes.

The manner in which the coupling member 58 attaches to the yoke rotate shaft 54 and the manner in which the weldment 160 attaches to the mounting pads 162, 164 (described above) permit a non-ECT scintillation camera having the remaining described structure to be conveniently and rapidly upgraded in the field to have the ECT drive capability.

Having thus described the invention with particular reference to the preferred forms of ECT drive struc- ture, it will be obvious to those skilled in the art to which the invention pertains, after understanding the invention, that various changes and modifications may be made therein without departing from the spirit and scope of the invention as defined by the claims appended hereto. Positional references of certain elements shown in the drawings (such as "left", "right", etc.) have been made throughout the specification merely to facilitate the explanation of the preferred embodiment, and such positional references should not be viewed as limiting the position which such elements may have in other embodiments. Similarly, it will be appreciated that the dimensions, shapes and layout of the various elements can be varied to suit individual tastes and requirements.

What is claimed is:

1. Supporting structure for driving a detector head of a radiation detector for emission computerized tomography, comprising an arm supporting the head adjacent an end thereof;

a base providing a fulcrum, the arm being moveably mounted on the base at the fulcrum;

means for counterbalancing the moment of the arm about the fulcrum due to the weight of the head; and means for driving the arm about the fulcrum so that the head traverses an arc with the head facing inward and so that a reference line drawn from the fulcrum to the head describes a conical surface having the fulcrum at its apex and the arc at its base.

2. Structure as defined in claim 1, wherein the driving means further comprises means mounted on the base and attached to the arm at a point displaced from the fulcrum for driving the point about the fulcrum so that the point traverses a second arc and so that a second reference line drawn from the fulcrum to the point describes a second conical surface having the fulcrum at its apex and the second arc at its base.

3. Structure as defined in claim 2, wherein the means for driving the point comprises a rotatable crank whose effective length is equal to the distance from the displaced point to the center of the second arc and which causes the second reference line to be tilted from a horizontal axis passing through the fulcrum by an angle of tilt which is dependent on the effective length of the crank.

4. Structure as defined in claim 3, further comprising means for varying the effective length of the crank whereby the angle of tilt of the arm about the fulcrum is correspondingly varied.

5. Structure as defined in claim 3, wherein the base comprises a column and a universal joint connecting the arm at the upper end of the column.

6. Structure as defined in claim 5, wherein the universal joint comprises a U-shaped saddle having two side members joined by a crosspiece rotatably mounted at the upper end of the column for movement about the column axis, and a tubular sleeve trunnioned between the side members for pivoting about a trunnion axis which is perpendicular to the column axis, and the arm comprises a shaft which is received within the sleeve for rotation about the sleeve axis.

7. Structure as defined in claim 4, wherein the crank comprises a screw, the crank is attached to the arm by coupling means including a nut held in threaded engagement with the screw and wherein the means for varying the effective length of the crank comprises means for rotating the screw relative to the nut to cause the nut to traverse the screw.

8. Structure as defined in claim 7, wherein the base comprises a column, a U-shaped saddle having two side members joined by a crosspiece rotatably mounted atop the column for movement about the column axis, and a tubular sleeve trunnioned between the side members for pivoting about a trunnion axis; the arm comprises a shaft which is received within the sleeve for rotation about the sleeve axis and having a free end; and the coupling means includes a telescoping member joining the free end of the shaft to the nut and serving to accommodate relative displacement of the end of the shaft and the nut along a direction parallel to the shaft axis as the position of the nut on the screw is varied.

9. Structure as defined in claim 8, wherein the telescoping member comprises a bifurcated body member fixed to the free end of the shaft and at least one slider plate pivotally attached to the nut and means slideably connecting the slider plate to the body member for relative movement of the plate parallel to the bifurcations of the body member.

10. Structure as defined in claim 9, wherein the slideably connecting means comprises a plurality of cam rollers between which the slider plate is received.

* * * * *